US008257079B1

(12) United States Patent  (10) Patent No.: US 8,257,079 B1
Plowman  (45) Date of Patent: Sep. 4, 2012

(54) ORTHODONTIC APPLIANCE

(76) Inventor: Paul E. Plowman, Oklahoma City, OK (US)

(*) Notice: Subject to any disclaimer, the term of this patent is extended or adjusted under 35 U.S.C. 154(b) by 316 days.

(21) Appl. No.: 12/057,096

(22) Filed: Mar. 27, 2008

(51) Int. Cl.
*A61C 3/00* (2006.01)

(52) U.S. Cl. .......................................... 433/18

(58) Field of Classification Search ............. 433/2, 8–9, 433/18–19, 24, 215, 229; 128/848
See application file for complete search history.

(56) References Cited

U.S. PATENT DOCUMENTS

| | | | |
|---|---|---|---|
| 3,513,838 A * | 5/1970 | Dammermann et al. ..... | 128/861 |
| 4,439,149 A | 3/1984 | Devincenzo | |
| 4,472,139 A * | 9/1984 | Rosenberg ...................... | 433/19 |
| 4,509,918 A | 4/1985 | Clark | |
| 4,619,609 A * | 10/1986 | Clark ................................ | 433/6 |
| 4,671,766 A | 6/1987 | Norton | |
| 4,950,158 A * | 8/1990 | Barngrover et al. ............ | 433/11 |
| 5,324,196 A * | 6/1994 | Magill ............................. | 433/19 |
| 5,443,384 A * | 8/1995 | Franseen et al. ................ | 433/18 |
| 5,564,927 A * | 10/1996 | Barnes et al. ................. | 433/179 |
| 5,683,244 A * | 11/1997 | Truax ............................... | 433/6 |
| 5,848,891 A * | 12/1998 | Eckhart et al. .................. | 433/19 |
| 5,871,350 A | 2/1999 | Clark et al. | |
| 5,964,587 A * | 10/1999 | Sato ................................ | 433/6 |
| 6,099,304 A * | 8/2000 | Carter ............................. | 433/19 |
| 6,368,106 B1 | 4/2002 | Clark | |
| 6,604,527 B1 * | 8/2003 | Palmisano .................... | 128/848 |
| 6,932,598 B1 * | 8/2005 | Anderson ....................... | 433/19 |
| 6,983,752 B2 * | 1/2006 | Garabadian .................. | 128/848 |
| 7,018,203 B2 | 3/2006 | Clark | |
| 7,226,287 B2 * | 6/2007 | Abels et al. .................... | 433/18 |
| 7,293,987 B2 * | 11/2007 | Abels et al. .................... | 433/18 |
| 7,637,262 B2 * | 12/2009 | Bailey .......................... | 128/848 |
| 2003/0031976 A1* | 2/2003 | Clark ............................. | 433/19 |
| 2005/0244778 A1* | 11/2005 | Abels et al. .................... | 433/18 |
| 2005/0244779 A1* | 11/2005 | Abels et al. .................... | 433/18 |
| 2006/0014117 A1* | 1/2006 | Abels et al. .................... | 433/18 |
| 2007/0111153 A1* | 5/2007 | Abels et al. .................... | 433/18 |
| 2008/0102414 A1* | 5/2008 | Abels et al. .................... | 433/19 |

* cited by examiner

*Primary Examiner* — Cris L Rodriguez
*Assistant Examiner* — Hao D Mai
(74) *Attorney, Agent, or Firm* — Hall Estill Attorneys at Law; Daniel P. Dooley

(57) ABSTRACT

A dental appliance that includes at least a first member presenting a first sloped surface and configured for attachment to a first tooth of a patient. Preferably, the first member interacts with a second member presenting a second sloped surface and configured for attachment to a second tooth of the patient. The preferred embodiment includes the interaction between the first and second member's sloped surfaces re-align the patient's jaw to correct mandibular disharmonies. In the preferred embodiment, each of the first and second members includes a laterally extending extraction feature to facilitate separation of the first and second members from the patient's teeth.

6 Claims, 9 Drawing Sheets

ORTHODONTIC APPLIANCE

FIELD OF THE INVENTION

The present invention relates generally to the field of orthodontic equipment and treatments, but not by way of limitation, to the correction of mandibular disharmonies.

BACKGROUND OF THE INVENTION

The ability to safely and efficiently correct dental disharmonies such as malocclusion has been a continued goal in the practice of orthodontic medicine.

Historically, dental disharmonies have been treated with a variety of techniques and devices. Disharmonies such as class II malocclusion have been corrected with complex apparatus that focus force on the mandible to gradually adjust its position in the tempromandibular joint. Likewise, corrective techniques have required continual supervision by a professional to ensure proper adjustment of the mandible. The lack of an efficient appliance to correct dental disharmonies results from the complexity of installation, use, and removal of the corrective appliance. With numerous pieces and precise locations in a mouth, common corrective appliances require operational harmony that is difficult to achieve for long periods due to everyday activities of a patient such as eating. Similarly, large corrective apparatus create occupational problems such as speaking and swallowing.

Many attempts have been made to provide a dental correction appliance to correct mandibular disharmonies including U.S. Pat. Nos. 7,018,203 and 6,604,527. However, none of the disclosed appliances provide an efficient method of installation, use, and removal that allows the patient to maintain a level of everyday activity. The U.S. Pat. No. 7,018,203 uses angled surfaces to correct class II malocclusion, but uses large "removable" components that require numerous connection features that restrict movement of the mouth unnecessarily. Moreover, U.S. Pat. No. 6,604,527 advances a mandible, but occupies all the teeth in the mouth which restricts a patient's ability to where the apparatus continually. Therefore, attempts have been made to correct mandibular disharmonies, but have failed to provide an appliance that is installed, used, and removed in a simple and efficient manner.

Accordingly, there is a continuing need for improved appliances to correct mandibular disharmonies.

SUMMARY OF THE INVENTION

In accordance with the preferred embodiments, an orthodontic appliance ("dental appliance") that includes at least a first member. The first member having a first sloped surface and is configured to attach to a tooth. In a preferred embodiment, a second member has a second sloped surface and is configured to attach to a tooth. The sloped surface of the second member preferably interacts with the sloped surface of the first member to correct mandibular disharmony. Further in a preferred embodiment, the first and second members each have a laterally extending extraction feature extending from a main body portion. The laterally extending extraction features facilitate separation of the first and second members from the patient's teeth.

DETAILED DESCRIPTION OF THE INVENTION

Preferred embodiments of the present invention are generally directed to a dental appliance configured to provide treatment of mandibular disharmonies, such as Class II malocclusions and rearward divergent mandibles.

Figure 1:
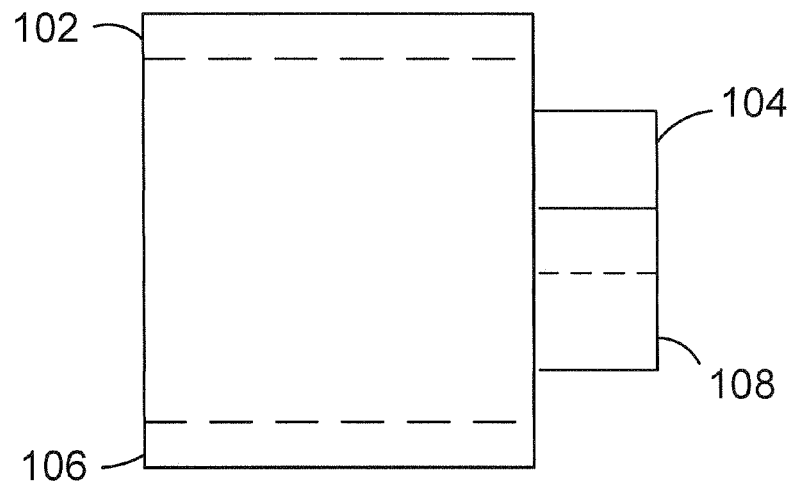
FIG. 1 is a front view of the dental appliance in a preferred embodiment.

FIG. 1 shows a front view of the orthodontic appliance 100 (also referred to herein as dental appliance 100) in a preferred embodiment. The dental appliance 100 preferably includes a first member 102 with a main body portion to which a first extraction feature 104 laterally extends. A second member 106 is preferably shown in close proximity to the first member 102. In a preferred embodiment, the second member 106 has a main body portion to which a laterally extending second extraction feature 108.

Figure 2:
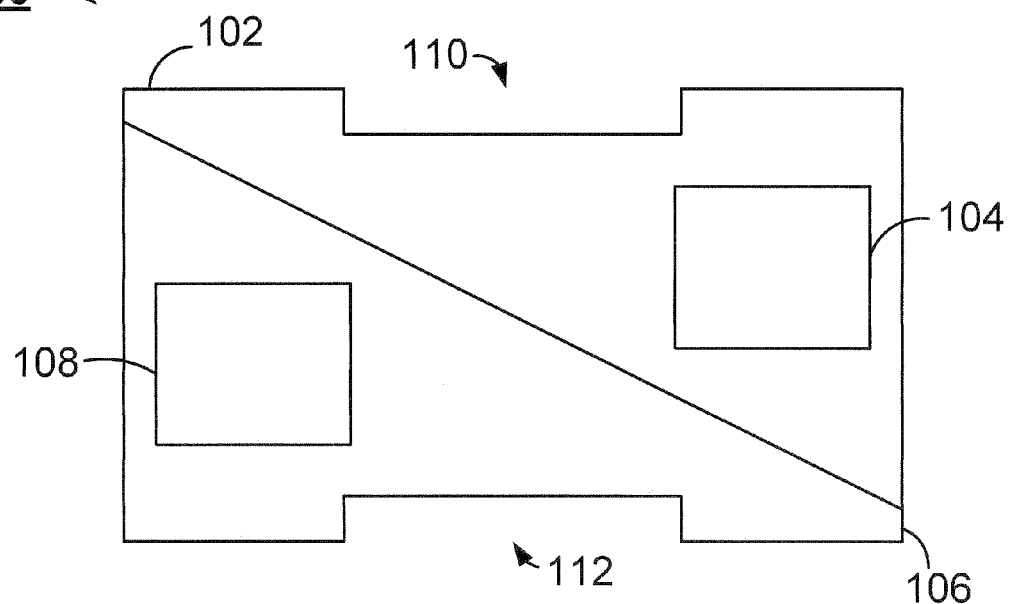
FIG. 2 is a side view of the dental appliance in a preferred embodiment.

FIG. 2 displays a side view of the dental appliance 100 in a preferred embodiment. The dental appliance 100 includes a first member 102 and a second member 106 in close proximity. Preferably, the first and second members 102 and 106 can be a variety of sizes to best facilitate correction of a mandibular disharmony. A first extraction feature 104 is shown laterally extending from the first member 102 while a second extraction feature 108 laterally extends from the second member 106. In a preferred embodiment, the first member 102 includes a first securement well 110. Similarly, the second member 106 preferably includes a second securement well 112.

Figure 3:
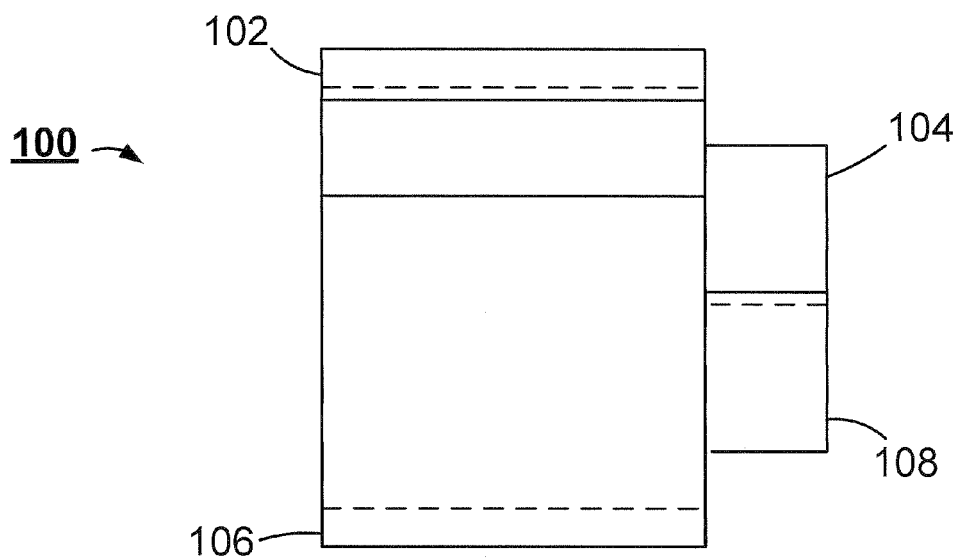
FIG. 3 is a front view of the dental appliance in a preferred embodiment.

The illustration of FIG. 3 shows a front view of the dental appliance 100 in a preferred embodiment. The first member 102 is displayed preferably separated from the second member 106. A first extraction feature 104 is illustrated as laterally extending from the main body portion of the first member 102. A second extraction feature 108 is preferably shown laterally extending from the main body portion of the second member 106.

Figure 4:
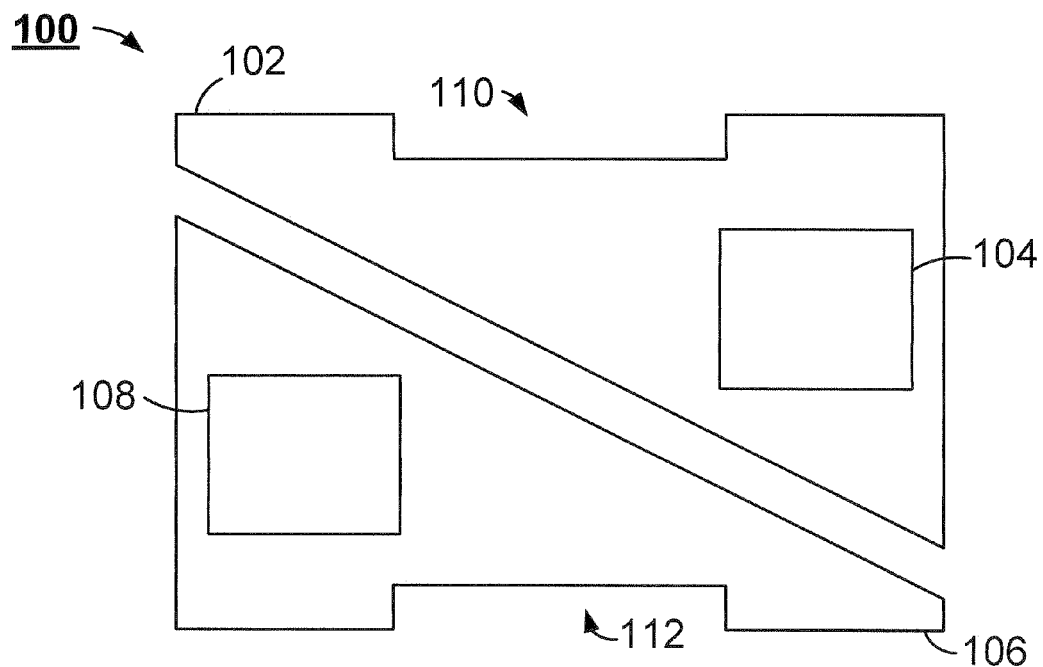
FIG. 4 is a side view of the dental appliance in a preferred embodiment.

The side view of the preferred embodiment of the dental appliance 100 is displayed in FIG. 4. The first member 102 is displayed preferably separated from the second member 106. A first extraction feature 104 is illustrated as laterally extending from the main body portion of the first member 102 while a second extraction feature 108 is shown laterally extending from the main body portion of the second member 106. In a preferred embodiment, the first member 102 includes a first securement well 110. Likewise, the second member 106 includes a second securement well 112.

Figure 5:
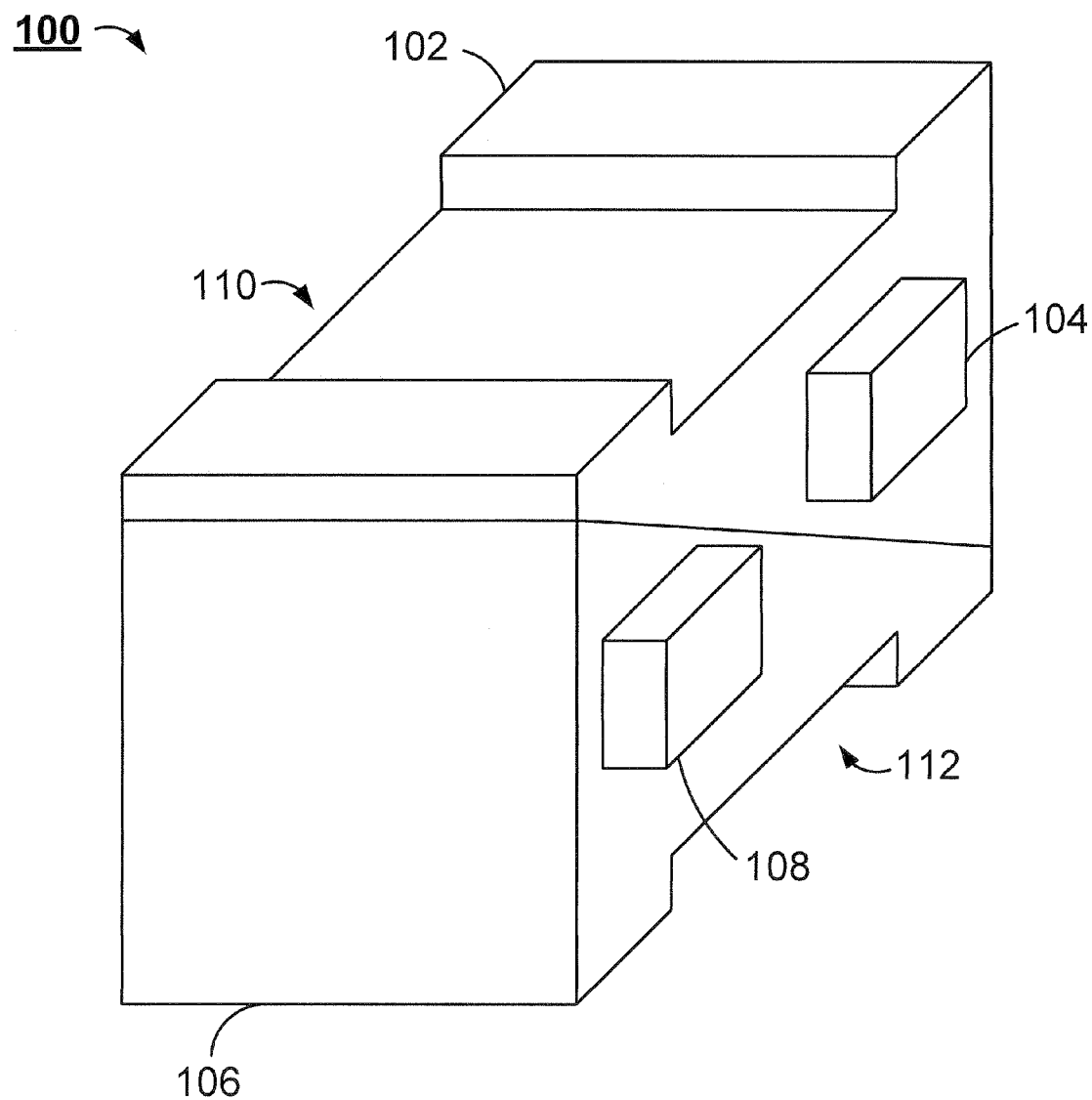
FIG. 5 is an isometric view of the dental appliance in a preferred embodiment.

FIG. 5 displays an isometric view of a preferred embodiment of the dental appliance 100. A first member 102 is shown with a main body portion having a laterally extending first extraction feature 104. A second member 106 is illustrated in close proximity to the first member 102 while including a second extraction feature 108 that laterally extends from the main body portion of the second member 106. Preferably, a first securement well 110 is included in the first member 102. Further, a second securement well 112 is included in the second member 106

Figure 6:
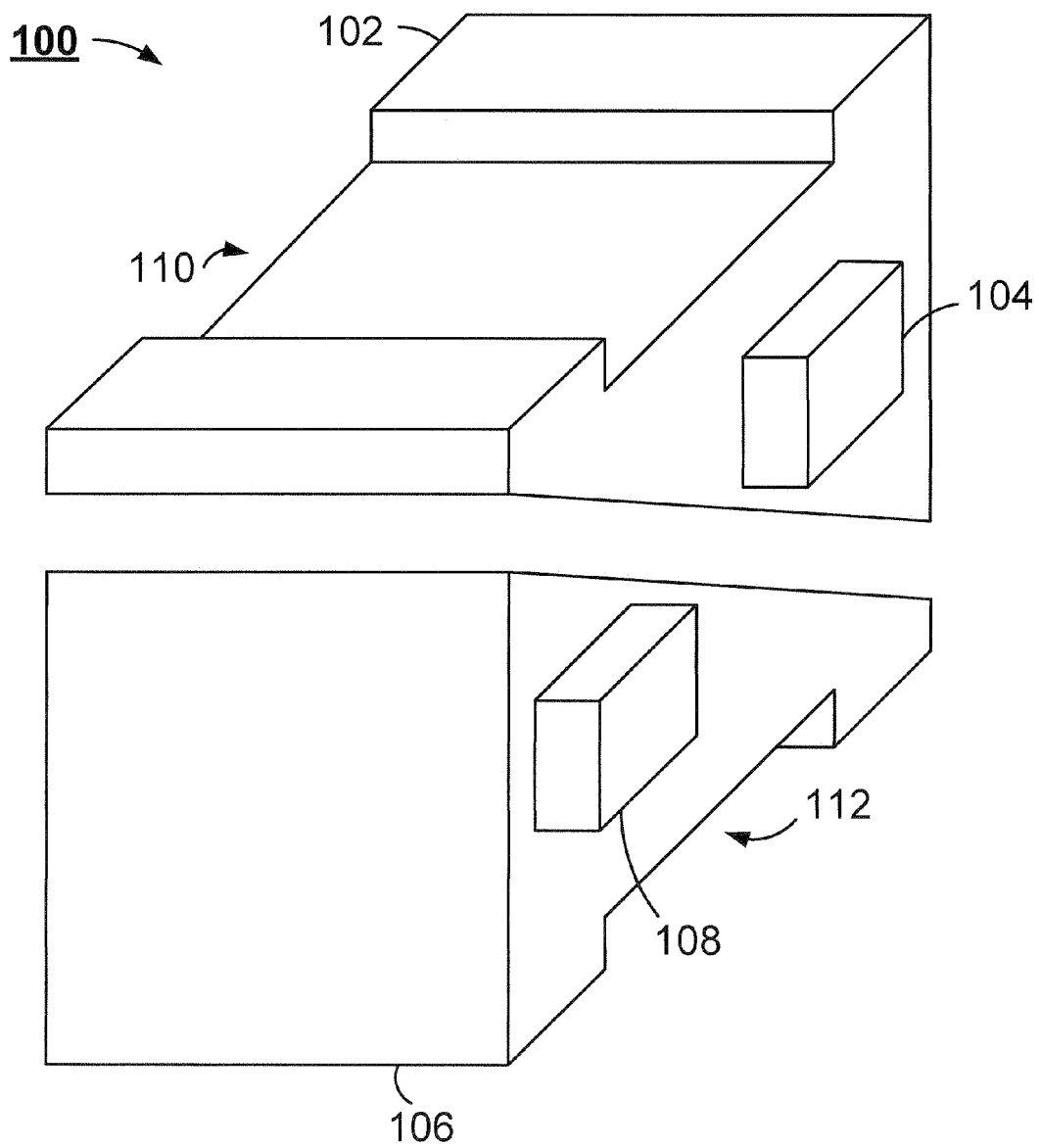
FIG. 6 is an isometric view of the dental appliance in a preferred embodiment.

The illustration of FIG. 6 shows an isometric view of the preferred embodiment of the dental appliance 100. The first member 102 is displayed separated from the second member 106, but including a first extraction feature 104 laterally extending from the main body portion and a first securement well 110. Further in a preferred embodiment, the second member 106 includes a second extraction feature 108 extending from the main body portion and a second securement well 112. With large variations in the size of an individual's first molar tooth, the dental appliance 100 alternatively can have a variety of widths.

Figure 7:
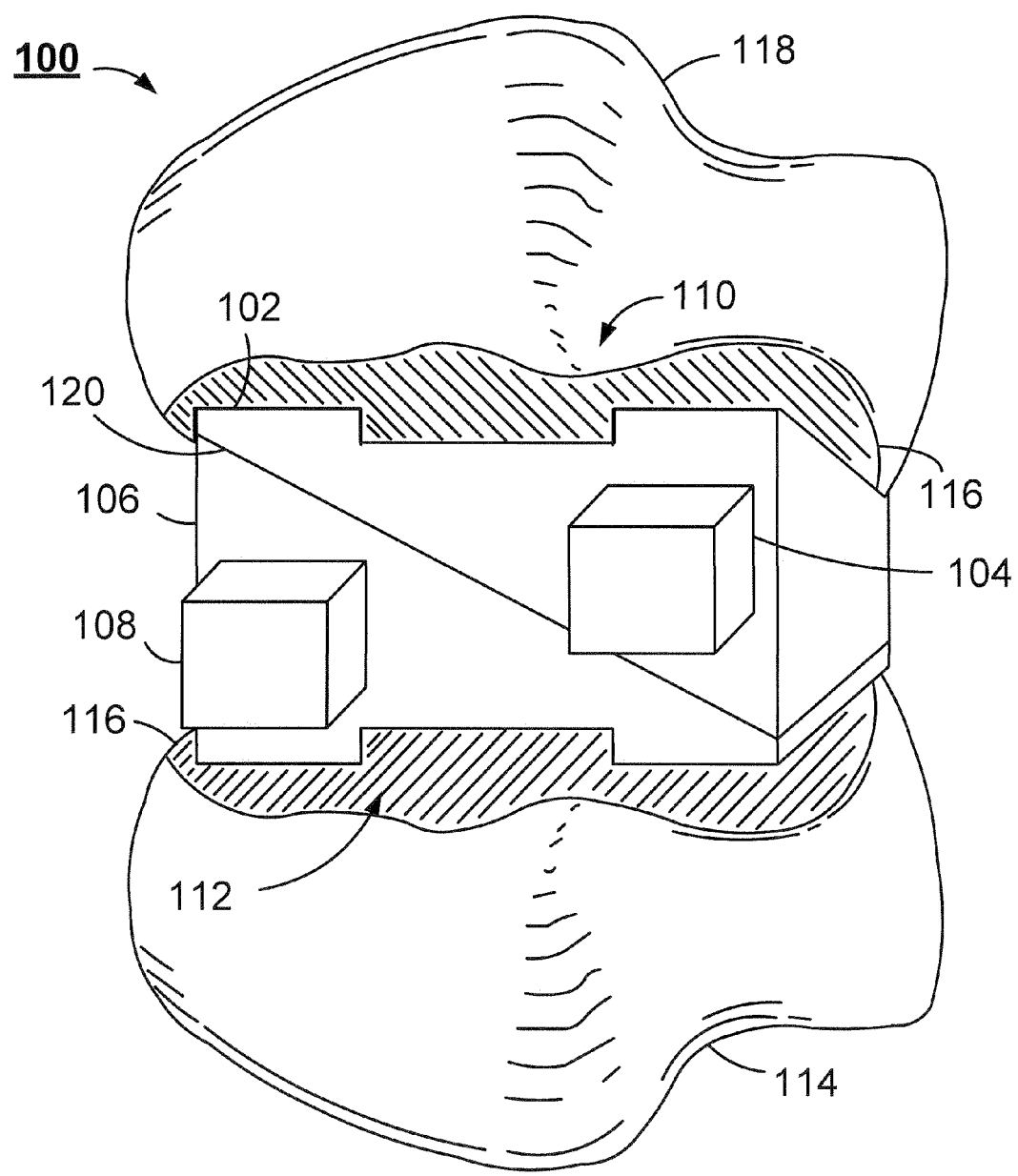
FIG. 7 is an isometric view of the dental appliance in a preferred embodiment shown in perspective.

FIG. 7 shows an isometric perspective view of the preferred embodiment of the dental appliance 100. In practice, the dental appliance 100 is installed, preferably, on the mandibular first molar 114 with adhesive 116 applied to the occlusional surface of the tooth as well as to the occlusional surface of the maxillary first molar 118 with adhesive 116. Thus, the second securement well 112 is filled with adhesive 116 and the second member 106, with its laterally extending second extraction feature 108, is secured to the mandiblular first molar 114. Preferably, the second member 106 is attached to the first member 102 with a temporary bonding agent 118. Further in a preferred embodiment, adhesive 116 is placed on the occlusional surface of the maxillary first molar. As the mandible is positioned in correct occlusional relationship with the maxilla, adhesive fills the first securement well 110 and secures the first member 102 to the maxillary first molar. Subsequently in a preferred embodiment, the temporary bonding agent 120 is removed and the first member 102 and second member 106 are operatively separated. The gradual correction of the mandibular disharmony occurs in the months following installation of the dental appliance 100 due to the interaction of the sloped surface of the first member 102 with the sloped surface of the second member 106 at all times including common occupational activities such as talking, chewing, and biting.

Figure 8:
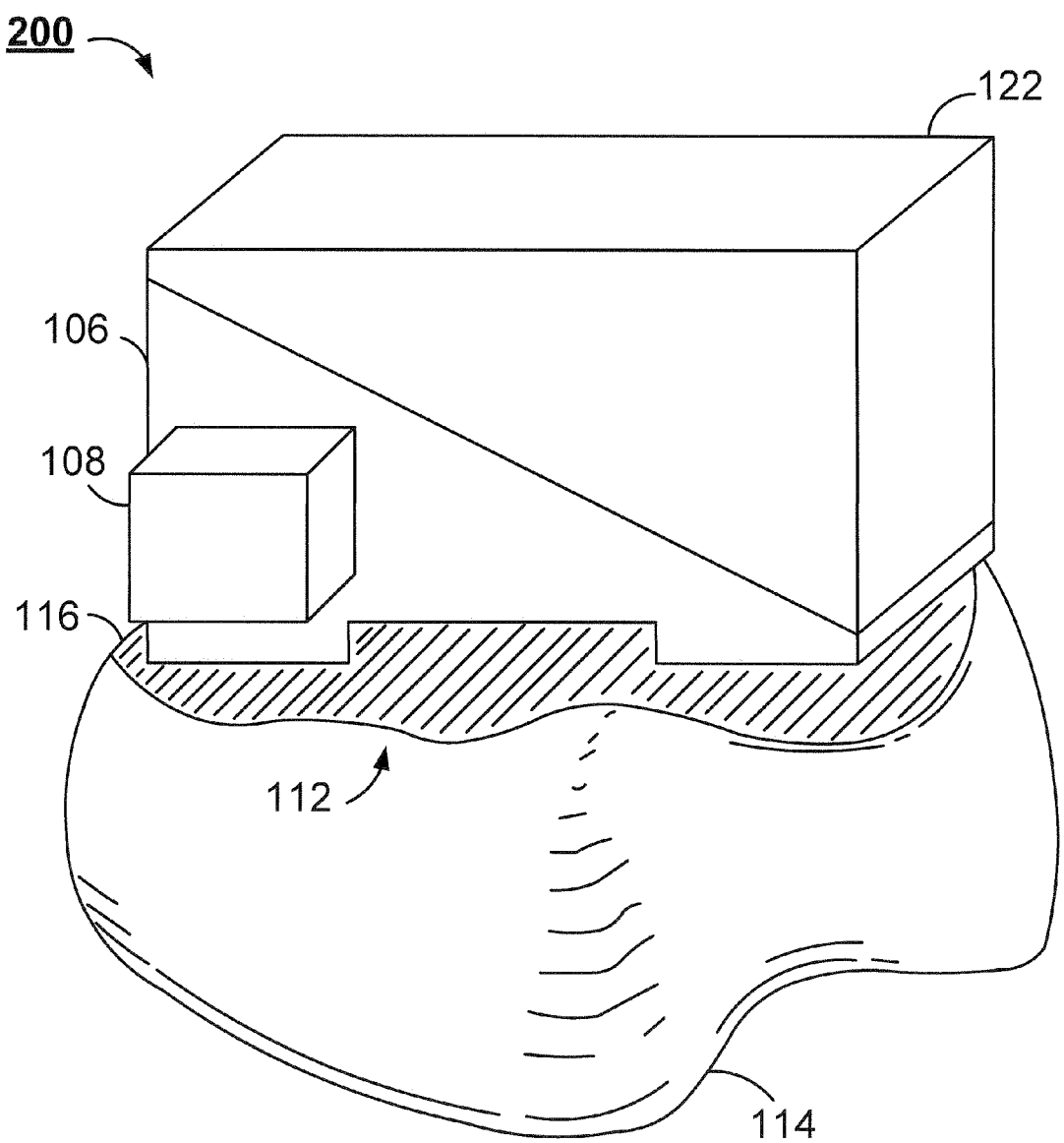
FIG. 8 is an isometric view of the dental appliance in an alternate embodiment shown in perspective.

An isometric view of an alternate embodiment of the dental appliance 200 is shown in FIG. 8. The alternate embodiment displayed includes the second member 106 secured to the mandibular first molar 114 with adhesive 116 filling the second securement well 112. Preferably, a temporary bonding agent 120 connects the second member 106 to a removal cleat 122 which can alternatively include a laterally extending third extraction feature.

Figure 9:
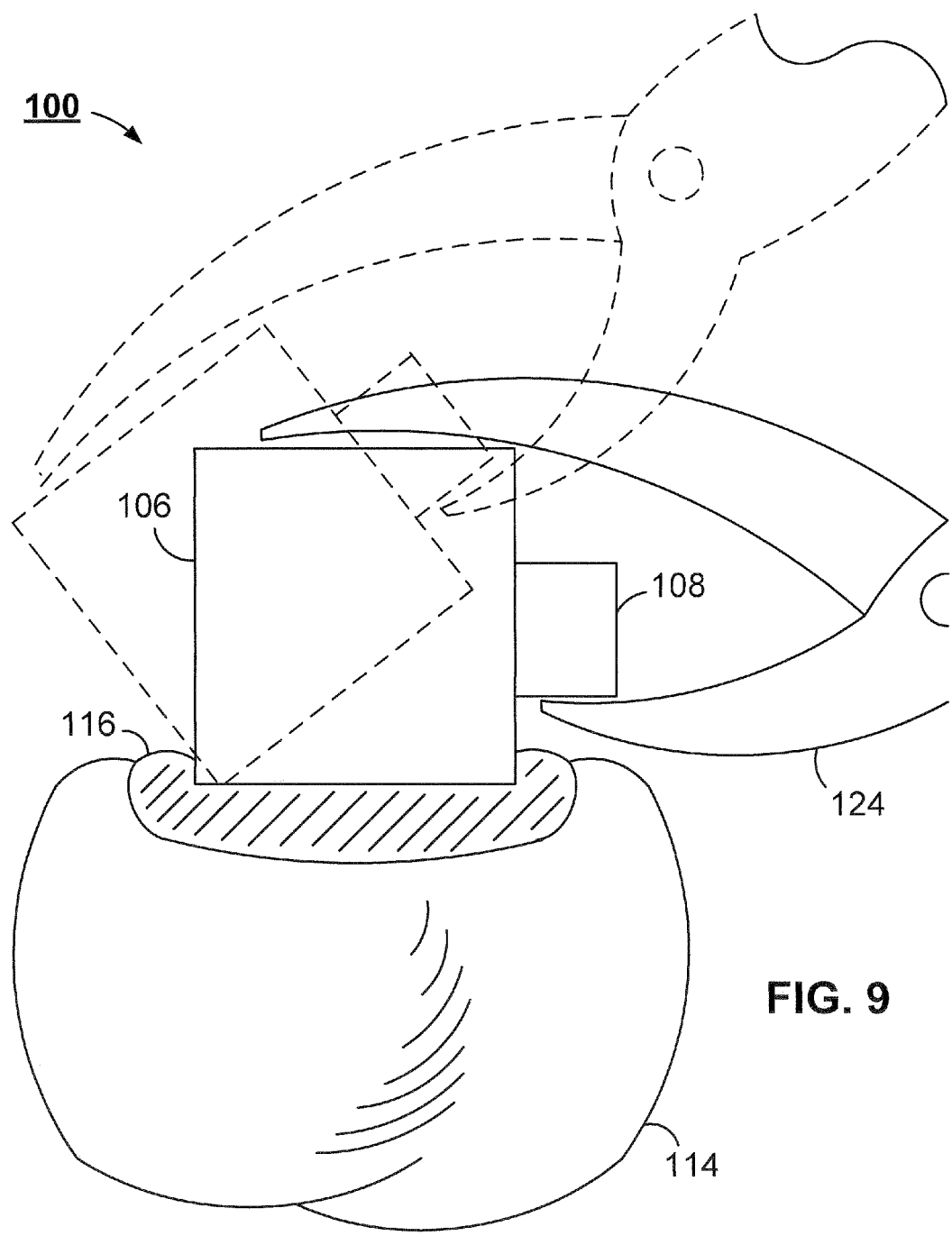
FIG. 9 is a front view of the dental appliance in a preferred embodiment shown in perspective.

FIG. 9 shows a front view in perspective of the preferred embodiment of the dental appliance 100. The preferred removal procedure is depicted with dashed lines. Further in a preferred embodiment, the second member 106 is displayed secured to the mandibular first molar 114 with adhesive 116. The laterally extending extraction feature 108 is preferably illustrated operatively engaged with a removal tool 124. The removal tool 124 can alternatively be a wide variety of instruments such as a chisel that can separate the second member 106 from the mandibular first molar 114. Also in an alternative embodiment, the removal cleat 122 can be connected to the second member 106 to provide a more efficient separation of the second member 106 with the mandibular first molar 114.

Preferably, the installation, use, and removal of the dental appliance 100 occupy only one tooth on both the mandibular and maxillary components of a mouth to facilitate the correction of mandibular disharmonies. The dental appliance can also be installed on the opposing mandibular first molar to provide symmetry across the mouth. Hence, an alternative embodiment includes a dental appliance 100 installed on both sides of the mouth that are secured to all the first molars of a mouth. Likewise, in an alternate embodiment the dental appliance 100 can be installed, used, and removed from a tooth other than the first molar singularly or in combination.

Figure 10:
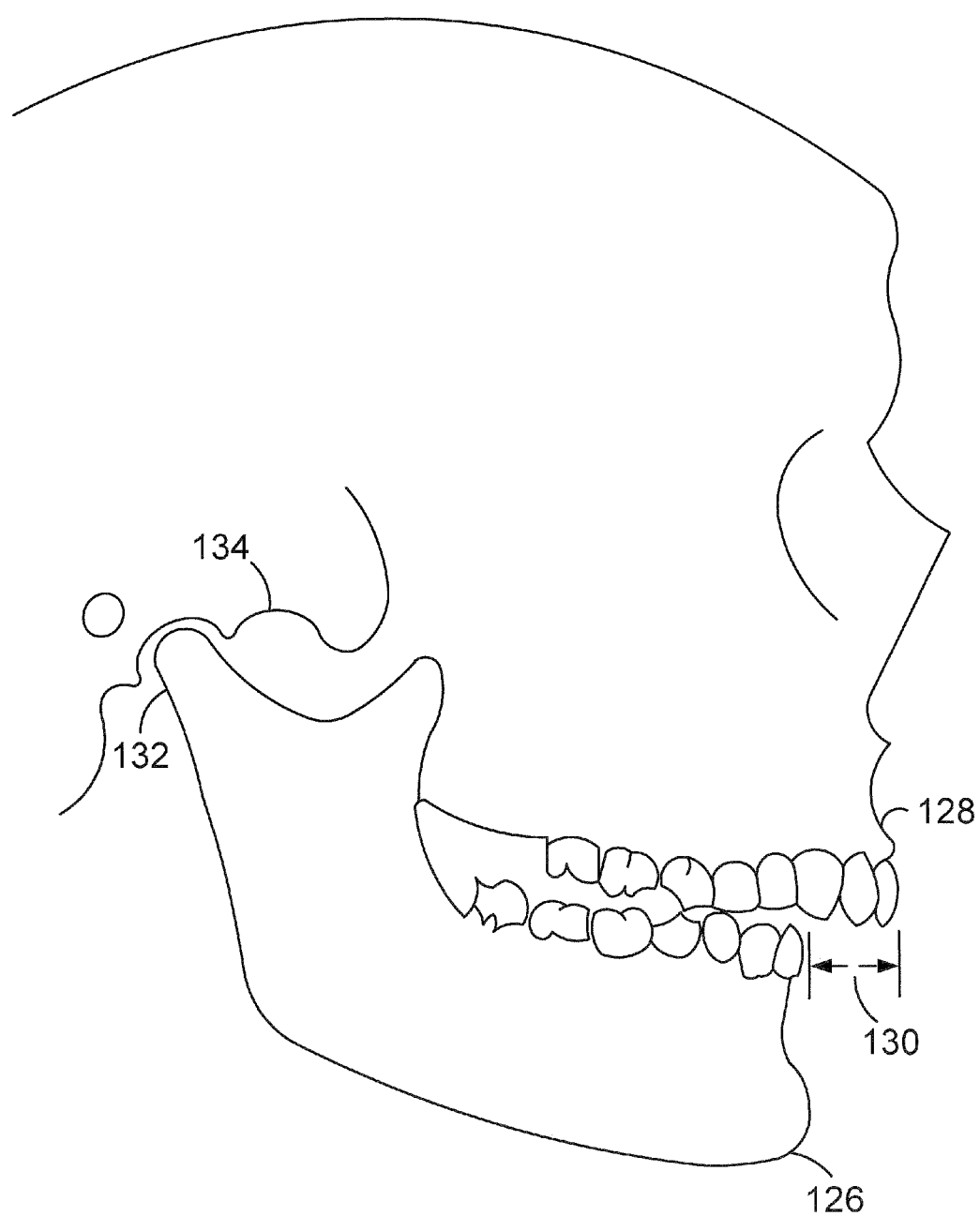
FIG. 10 is a side view of a mandibular disharmony.

FIG. 10 displays a side view of a mandibular disharmony. The mandible 126 is illustrated in malocclusion as an "overbite" or "buck-teeth." The mandibular disharmony displayed consists of the mandible 126 meeting the maxilla 128 in an operative manner where there exists a correction area 130. Continual use of the dental appliance 100 in either preferred or alternate embodiments will result in the correction area 130 gradually becoming smaller as the condyle 132 part of the mandible 126 is repositioned into the is correct position in the mandibular fossa 134.

Figure 11:
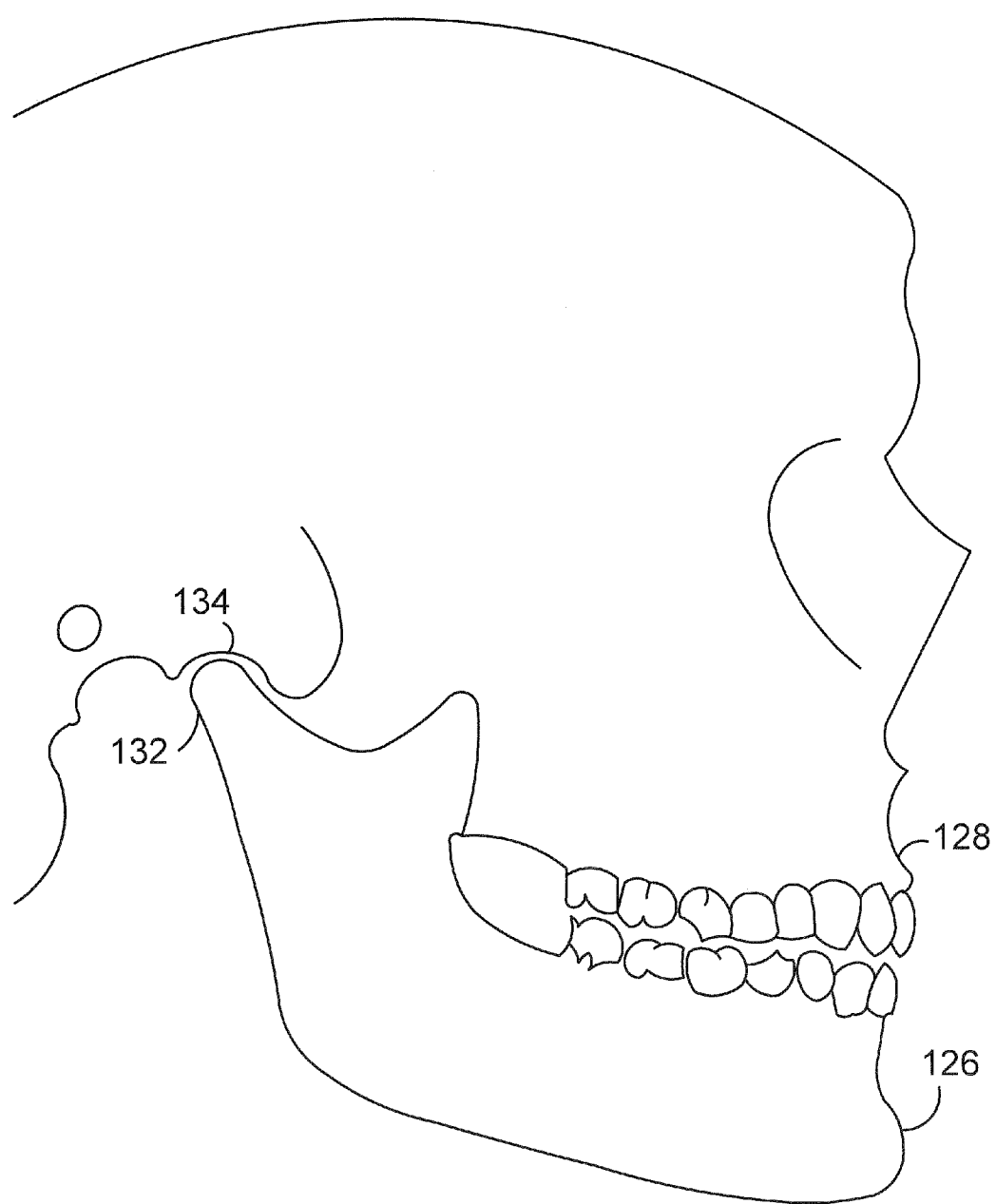
FIG. 11 is a side view of mandibular harmony.

A corrected mandibular disharmony is displayed from the side in FIG. 11. The correct position of the mandibular condyle 132 in the mandibular fossa 134 corresponds to the occlusional harmony between the teeth, mandible, and maxilla.

What is claimed is:

1. A dental appliance comprising:
a first main body having a length not greater than a length of a selected single first tooth of a patient, and a width consistent with a width of the selected single first tooth of the patient;
a first side extending along the length of the first main body;
a second side disposed on a side of the first main body opposite from the first side of the first main body and extending along the length of the first main body;
a first sloped surface disposed between the first and second sides, the first sloped surface extending along the entire width of the first main body between the first and second sides of the first main body, and the first sloped surface confined within a height, the length, and the width of the first main body;
a first securement well provided on a third side of the first main body, the third side opposite from the first sloped surface, the first securement well disposed between the first and second sides of the first main body, the first securement well extending along the entire width of the first main body between the first and second sides, and the first securement well confined within the height, length, and width of the first main body, wherein a length of the first securement well is less than the length of the selected single first tooth of a patient;
a first solid extraction feature extending from the first side of the first main body and positioned above the first securement well;
a second main body having a length not greater than a length of a selected single second tooth of a patient, and a width consistent with a width of the selected single second tooth of the patient;
a primary side extending along the length of the second main body;

a secondary side disposed on a side of the second main body opposite from the primary side of the second main body and extending along the length of the second main body;

a second sloped surface disposed between the primary and secondary sides, the second sloped surface extending along the entire width of the second main body between the primary and secondary sides of the second main body, and the second sloped surface confined within a height, the length, and the width of the second main body;

a second securement well provided on a third side of the second main body, the third side opposite from the second sloped surface, the second securement well disposed between the primary and secondary sides of the second main body, the second securement well extending along the entire width of the second main body between the primary and secondary sides, and the second securement well confined within the height, length, and width of the second main body, wherein a length of the second securement well is less than the length of the selected single second tooth of a patient; and a second solid extraction feature extending from the primary side of the second main body and positioned below the second securement well.

2. The appliance of claim 1, wherein the first main body is secured on the mandibular first molar on a selected side of the mouth of the patient.

3. The appliance of claim 1, wherein the second main body is secured to the corresponding maxillary first molar on the selected side of the mouth of the patient.

4. The appliance of claim 1, wherein both the first and second main bodies are secured to a predetermined corresponding set of mandibular and maxillary molars.

5. The appliance of claim 1, wherein the first and second main bodies form an operative pair, and further comprising a duplicate operative pair secured to respective corresponding teeth on the opposite side of the mouth.

6. The appliance of claim 1, wherein, the first and second main bodies have of different respective widths.

* * * * *